United States Patent [19]

Embry et al.

[11] Patent Number: 4,894,238
[45] Date of Patent: Jan. 16, 1990

[54] CONTROLLED RELEASE COMPOSITIONS

[75] Inventors: Mostyn P. Embry, Woodstock, Great Britain; Neil B. Graham, Bearsden, Scotland

[73] Assignee: National Research Development Corporation, London, England

[21] Appl. No.: 208,849

[22] Filed: Jun. 14, 1988

Related U.S. Application Data

[63] Continuation of Ser. No. 6,328, Jan. 14, 1987, abandoned, which is a continuation of Ser. No. 854,072, Apr. 17, 1986, abandoned, which is a continuation of Ser. No. 630,357, Jul. 16, 1984, abandoned, which is a continuation of Ser. No. 387,774, Jun. 14, 1982, abandoned, which is a continuation of Ser. No. 212,735, filed as PCT GB80/00049 on Mar. 21, 1980, published as WO80/01984 on Oct. 2, 1980, abandoned.

[30] Foreign Application Priority Data

Mar. 21, 1979 [GB] United Kingdom ................. 7909853

[51] Int. Cl.$^4$ ...................... A61K 47/00; A61K 9/00; A61K 9/02
[52] U.S. Cl. ..................................... 424/486; 424/422; 424/428; 424/433; 424/436
[58] Field of Search ................. 424/19, 422, 428, 433, 424/436, 486; 528/76–79, 90; 521/905

[56] References Cited

U.S. PATENT DOCUMENTS 3,822,238  7/1974  Blair ............................... 528/904 X
3,975,350  8/1976  Hudgin et al. ................. 260/30.4 N
4,352,790 10/1982  Johansson et al. ..................... 424/78

FOREIGN PATENT DOCUMENTS 2373279  7/1978  France .
1135966 12/1968  United Kingdom .................. 528/76
1486288  9/1977  United Kingdom .................. 528/76

OTHER PUBLICATIONS

Encyclopedia of Polymer Science and Technology, vol. 15, John Wiley, New York, 1971, p. 289.

Primary Examiner—Richard A. Schwartz
Attorney, Agent, or Firm—Oblon, Spivak, McClelland, Maier & Neustadt

[57] ABSTRACT

A controlled release composition comprising an active substance other than a prostaglandin and a polymeric carrier therefor comprising residues having a ratio of number average molecular weight to functionality greater than 1000 which comprises polyethylene oxide and are cross-linked through urethane groups.

18 Claims, No Drawings

CONTROLLED RELEASE COMPOSITIONS

This application is a continuation of application Ser. No. 07/006,328, filed on Jan. 14, 1987, now abandoned, which is a continuation of abandoned application of Ser. No. 854,072 filed Apr. 17, 1986 which in turn is a continuation of abandoned application Ser. No. 630,357 filed July 16, 1984 which in turn is a continuation of abandoned Ser. No. 387,774 filed June 14, 1982 which in turn is a continuation of abandoned application Ser. No. 212,735 filed as PCT GB80/00049 on Mar. 21, 1980, published as WO80/01984 on Oct. 2, 1980, now abandoned.

This invention relates to the formulation of active substances.

A considerable level of interest exists in the use of polymers as carriers in the formulation of various active substances. The main problem which arises with such a method of formulation is that the effecting release of the active substance from the polymer at an appropriate rate, and the polymer systems which have been proposed in the prior art are often not suited to the high level of control of release which is necessary for many applications such as the vaginal administration of pessaries for the induction of labour, as abortifacients, or in a contraceptive role.

It is an object of the present invention to provide a method of formulating a wide variety of active substances which utilises a polymer system having properties particularly suited to this purpose and selected for its particular value therein.

According to the present invention a controlled release composition comprises an active substance other than a prostaglandin and a polymeric carrier therefor comprising residues having a ratio of number average molecular weight to functionality greater than 1,000 which comprise polyethylene oxide and are cross-linked through urethane groups, preferably comprising a polymeric carrier comprising residues which comprise polyethylene oxide having a ratio of number average molecular weight to functionality greater than 1,000 and are cross-linked through urethane groups.

In our co-pending application we have described and claimed a controlled release composition comprising a prostaglandin and a polymeric carrier therefor comprising residues having a ratio of number average molecular weight to functionality greater than 1,000 which comprise polyethylene oxide and are cross-linked through urethane groups.

In this description the term equivalent weight is used as meaning the number average molecular weight ÷ functionality.

Residues comprising polyethylene oxide contain the repeat unit $(CH_2CH_2O)$ and are conveniently prepared by the stepwise addition of ethylene oxide to a compound containing a reactive hydrogen atom therein, for example the hydrogen atom of an aromatic or especially an aliphatic hydroxy, carboxy, amino or mercapto group, such as a phenolic group. Compounds of most interest contain two or more of such groups which may be the same or different, particular interest centering on carboxy and especially hydroxy groups. Preferred compounds for the preparation of the polyethylene oxides used in the present invention are thus polyhydroxy compounds containing particularly two but also three, four or on occasion, even more, hydroxy groups. In its simplest form, for example as prepared by the addition of ethylene oxide to ethylene glycol, polyethylene oxide has the difunctional structure

wherein n is an integer of varying size depending on the molecular weight of the polyethylene oxide, although various more complex forms may be prepared using other starting compounds and, in particular, forms of tri- or higher poly-functionality may be prepared using compounds containing more than two active hydrogen atoms.

However, the residues comprising the polyethylene oxide, typically prepared as aforesaid, may also comprise a minor amount of at least one additional component, for example, a higher poly(alkylene oxide) such as polypropylene oxide or polybutylene oxide, or a copolymerised higher alkylene oxide such as propylene oxide or butylene oxide. Typically, this minor amount will be small, suitably no more than 20%, preferably no more than 10% by weight or even less of the residue. Although the residues of equivalent weight greater than 1,000 preferably greater than 1,500, which comprise polyethylene oxide together with the urethane cross-linking component, do constitute that part of the polymeric carrier which is of particular importance and is responsible in large part for conferring to the polymeric carrier its desirable properties, it will be appreciated that the polymeric carrier may nevertheless, also incorporate at least one additional component. Such additional components may include blocks of other polymers which are introduced therein, particularly other polyalkylene oxides, for example polypropylene oxides and polybutylene oxides or polyethylene oxide of equivalent weight less than 1,000.

Such co-polymers are, however, generally of rather less interest since polyethylene oxide possesses unique properties among the polyalkylene oxides arising from its hydrophilic character which render it of particular value in the present invention.

It may also on occasion be desirable to effect chain extension and a consequent increase in the degree of swelling which is thereby obtained. Such chain extension may be effected by the incorporation of polyethylene oxide of equivalent weight less than 1,000 or other diols in the reaction mixture containing the high equivalent weight polyethylene oxide and the urethane cross-link predcursors, for example low molecular weight aliphatic or aromatic dihydroxy compounds. As well as effecting swelling, such chain extension can have a beneficial effect on the physical strength of the polymer, both when wet and when dry.

It is an important feature of the polymers used in the present invention that they are cross-linked through urethane groups. Cross-linking is necessary to produce a polymer which is water swellable rather than water soluble and at the same time confers greater cohesion in the swollen polymer. Such cross linking gives a system which may be regarded, in theory, as having an infinite molecular weight, and a significant degree of cross-linking is required to achieve this. The preferred degree of cross-linking corresponds to a range of from three cross-linking points per residue comprising polyethylene oxide to one cross-linking point per ten such residues, particularly from one or two cross-linking points per residue to one cross-linking point per four or five residues. Alternatively, the preferred degree of cross-linking can in many cases be described as that leading to a molecular weight between cross-linking points of from about $\frac{1}{3}\times$(number average molecular weight of isocyanate + number average molecular weight of polyethylene oxide) to 10×(the sum of these molecular weights), particularly from ½ or 1× to 4 or 5×(the sum of these molecular weights).

While the polymeric carrier is required to swell rather than dissolve in water, it may contain a water-extractable fraction which is preferably a minor proportion by weight which can be as high as 30-40% by weight without detracting from the useful properties of the composition. More usually, however, the water-extractable fraction is 25% by weight or less. It will be appreciated, however, that it is the non-water extractable portion which is responsible in large part for the desirable release characteristics and, accordingly, it may be in many instances preferable to extract the polymer after preparation with water or a water/organic solvent mixture to substantially remove any extractable portion leaving, for example, no more than 5% or 10% by weight of such a portion. Thus, in the case of a composition for use in humans, it is desirable that substantially all water-extractable material is absent and the whole of the polymeric carrier in the composition is substantially insoluble. This is also desirable, in general, in order to give the best resproducibility of release for the drug or other active material contained in a composition.

The detailed method of cross-linking may vary quite widely although all methods basically involve the attachment of the residues comprising polyethylene oxide through a urethane group thus:

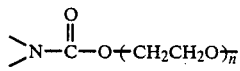

A preferred method comprises the reaction of polyethylene oxide of equivalent weight greater than 1,000, preferably greater than 1,500 with a poly-functional isocyanate, including aromatic di-isocyanates such as 2,4 and/or 2,6 toluene di-isocyanate; aliphatic di-isocynates such as 1,6-hexamethylene di-isocynate, isophorone di-isocyanate, 4,4'-dicyclohexyl methane di-isocyanate, and cyclohexylene 1,2- and 1,4-di-isocyanate; and araliphatic di-isocyanates such as 4,4'-diphenylmethane di-isocyanate, particularly aliphatic di-isocyanates.

When reacting a di-isocyanate with a polyethylene oxide it is preferred to incorporate an additional polyfunctional compound in the reactants to give the desired cross-linking. Tri- or higher functional amines and particularly hydroxy compounds are conveniently used, including aliphatic triols such as 2-ethyl-2-hydroxymethyl propane-1,3-diol and 1,2,6-hexane-triol, aromatic triols such as phloroglucinol and pyrogallol, as well as araliphatic triols. The triol 1,2,6-hexane triol in particular has been found to given particularly attractive polymers, especially when used in connection with an araliphatic di-isocyanate such as 4,4'-diphenylmethane di-isocyanate or an aliphatic di-isocyanate. It will be appreciated, however, that a large class of low molecular weight polyols suitable for cross-linking in the polymers of the present invention is commercially available for the manufacture of rigid and flexible urethane foams. These materials are well known to those skilled in the art and comprise oxypropylated triols, tetrols and sugars, as well as some polyesters. In general, low molecular weight materials are preferred as the higher molecular weights can give compatibility problems which make the preparation of the polymeric carriers much more difficult.

As an alternative to the incorporation of an added reactant as described above, cross-linking may be effected by the use of a tri- or higher polyfunctional isocyanate, either in pure form or as a component of a commercial isocyanate preparation containing both di- and tri-isocyanates. A further method of effecting the cross-linking is through the use of an excess of isocyanate which will result in cross-linking through the formation of an allophanate group. A yet further method of cross-linking consists of the formation of a prepolymer between the polyethylene oxide and a polyfunctional, for example trifunctional, isocyanate which contains free isocyanate groups, the pre-polymer then being cross-linked through the action of water with the formation of substituted urea groups.

It will be appreciated that the polymer may be produced using various proportions of polyethylene oxide to polyfunctional isocyanate depending on the type of cross-linking intended and other components used. In general, however, the amount of an isocyanate used is often equal to from 0.8 to 2.5 times its equivalent weight for each equivalent weight of polyethylene oxide, particularly from 0.9 to 1.3 times the equivalent weight of the isocyanate. When using a trihydroxy compound or other similar cross-linking inducing agent various proportions of this may again be used, but the amount of triol is often equal to from one tenth of a mole to three moles for each mole of the polyethylene oxide, particularly from one fifth or one fourth of a mole to one or two moles of the triol. If a triol or similar compound is included in the reactants than the amount of isocyanate used is increased, this amount then corresponding in many cases to the range indicated above but with the amount being related both to the polyethylene oxide and to the triol, i.e. 0.8 to 2.5 times and particularly 0.9 to 1.3 times the equivalent weight of the isocyanate for each equivalent weight of polyethylene oxide and an amount in a similar range for each equivalent weight of the triol.

The particular value of the cross-linked polyethylene oxide polymers used in the formulation of controlled release compositions according to the present invention lies in two quite unexpected discoveries which have been made in respect of the properties of these polymers.

The first of these unexpected properties is the ability of the polymers to form crystalline hydrogels. The term hydrogen is used in this specification to denote a polymer which is swellable by water to form a gel rather than being dissolved to form a solution, the term being applicable to the polymer either in the unswollen or dry state or in the swollen or wet state. Crystalline linear polyethylene oxides are known but it is surprising that gels having a high level of crystallinity are obtainable from polymers used in the present invention in view of the cross-linking therein. The existence of crystallites in the gels not only makes a significant contribution to the strength of the swollen gels but is also believed to be responsible in large part for the advantageous pattern of release shown by the polymeric carriers in the dry form for an active substance incorporated therein and as discussed hereinafter. It should be stressed that complete crystallinity is not necessary and, indeed, is generally unobtainable in practice even for linear polyethylene oxides. Thus, for example, the polymer prepared from PEG 6,000, 2-ethyl-2-hydroxymethylpropane-1,3- diol (0.5 molar proportion) and 4,4-diphenylmethane di-isocyanate as described in detail hereinafter has a crystallinity in the dry form, as determined by differential scanning calorimetry, which is approximately 40% of that of high molecular weight commercial linear polyethylene oxide homopolymer, a level which is however surprising in itself. Preferred levels of crystallinity at 20° C. are 5% or more, for example 10 or 20% or more, referred to a similar standard.

The second of the unexpected properties of the polymers used according to the present invention is their property of exhibiting a very considerable level of syneresis when the temperature of the water swollen polymer is raised. It is known that at room temperature insoluble polyethylene oxide will swell in water, the degree of swelling decreasing with increasing temperature. It has now been discovered that polymers used according to the present invention will swell at temperatures below 50° C. by absorbing water as such or from aqueous organic solvent, for example aqueous alcoholic solutions, or formamide, swelling by absorption of up to 1,000 parts per hundred of the original dry volume being attainable, and that, surprisingly, when the swollen polymer is heated, it shrinks, expelling some of the absorbed liquid. This property we believe to provide a counterpart to the function of crystallinity in controlling the behaviour of the polymeric carriers in the dry form and believe it to be responsible for the advantageous pattern of release shown by the polymeric carriers in the wet form, as discussed below.

It has been found that both the ability to crystallise, which is of importance in the case of the dry hydrogels, and the ability to shown syneresis, which is of importance in the wet hydrogels, is dependent on the equivalent weight of the residues comprising polyethylene oxide in the polymeric carrier. Thus, the presence of a sufficiently high equivalent weight will lead either to the crystallisation of the molecular chains which is present in the dry gels or to the formation of the hydrate chains which are present in the wet gels and which is believed to be responsible for the phenomenon of syneresis exhibited by these gels. We have found that both properties depend on the presence in the polymeric carrier of residues comprising polyethylene oxide units having an equivalent weight of greater than 1,000, for example of 1,200, suitably greater than 1,500, for example of 1,700, 1,800 or more, conveniently of about 2,000 or more and particularly 2,500 or 3,000 or more. Indeed, very high equivalent weights are quite acceptable, the upper limit substantially being governed by the availability of polyethylene oxide of these high equivalent weights; at the present time polymers of equivalent weights of as much as 10,000 being available for use. It is generally the case that unless steps are taken to avoid crystallisation, which would give products of less interest but which are nevertheless not excluded from the scope of the present invention, then the use of residues comprising polyethylene oxide of the equivalent weights indicated will lead to the presence of some proportion of crystallinity in the dry hydrogels. Reduction of the proportion of polyethylene oxide in the polymer through incorporation of high levels of the cross-linking agent or of other components will in general lead to reduction in the level of crystallinity and, accordingly, it is preferred that the proportion by weight of polyethylene oxide of equivalent weight above 1,500 in the polymer is at least 50% and preferably more than this, conveniently greater than 70% and conveniently as high as 75, 80, 85 or 90% more depending on the individual polymer, for example even up to 96 ot 98%.

The present invention is of broad applicability in the formulation of active substances, particularly biologically active substances. Example of classes of biologically active substances which may be incorporated in compositions of the present invention include pharmaceuticals, bacteriostats, viruscides, insecticides, herbicides, larvicides, fungicides, algaecides, nematocides, topical or dermatological agents, antifoulants, for marine growth prevention, enzymes and preservatives. Of particular interest are compositions of the present invention comprising, as biologically active substance, at least one pharmaceutical.

The compositions of this invention thus find wide application in medical and surgical, including veterinary, contexts and in horticulture and agriculture as well as outside these areas.

There is no necessity for the active substance to be water soluble although it will often possess some degree of water solubility; all that is required is that it is soluble to an extent commensurate with its desired concentration (which, in the case of a biologically active substance, is related to this activity) in the controlled release composition of this invention in the water or organic solvent used to swell the polymeric carrier on incorporation of the active substance therein.

Specific classes of drug which may be utilised in a controlled release composition of the invention include abortifacients other than prostaglandins, hypnotics, sedatives, tranquilisers, anti-pyretics, anti-inflammatory agents, anti-histamines, anti-tussives, anticonvulsants, muscle relaxants, anti-tumour agents, for example those for the treatment of malignant neoplasia, local anaesthetics, anti-Parkinson agents, topical or dermatological agents, diuretics, for example those containing potassium, such as potassium iodide, preparations, other than those containing prostaglandins, for the treatment of mental illness, for example preparations containing lithium for use in the treatment of manic depression, anti-spasmodics, anti-ulcer agents, preparations containing various substances for the treatment of infection by pathogens including anti-fungal agents, for example metronidazole, anti-parasitic agents and other anti-microbials, anti-malarials, cardiovascular agents, preprations containing hormones, for example androgenic, estroginic and progestational hormones, notably steroids such as oestradiol, sympathomimetic agents, hypoglycaemic agents, contraceptives, nutritional agents, preprations containing enzymes of various types of activity, for example chymotrypsin, preparations containing analgesics, for example aspirin, and agents with many other types of action including nematocides and other agents of veterinary application. Mixtures of active substances may be incorporated into the polymeric carrier.

The active substances may be incorporated into the polymer with this in dispersed form but is more preferably incorprated into the polymeric carrier after this has been formed into an appropriate physical format. Accordingly, the usual procedure for incorporation of the biologically active substance is for the polymer, in suitable physical form, to be swelled using a solution containing the substance to be incorporated. This solution may often be aqueous but may incorporate organic solvents for example alcohols such as ethyl alcohol in order to solubilise the substance and also in view of the improved swelling characteristics of such mixtures, and in some instances a completely non-aqueous organic solvent such as chloroform, ethanol/chloroform, tetrahydronaphthalene, nitrobenzene, methyl benzoate, butyrolactone or benzyl alcohol may be used. After swelling and absorption of the active substance, the release composition may be dried to remove the solvent or alternatively may be used in the swollen form. It has been found that the swelling procedure, and in particular the proportion of swelling relative to the original volume which is allowed to take place, can have a quite significant effect upon the subsequent behavior of the release composition in vivo, even though it may be dried before use. Preferably, therefore, the degree of swelling during incorporation of the biologically active substance lies between 150 parts per hundred and 700 parts per hundred of the original dry volume, particularly between 200 and 500 parts per hundred.

As indicated previously, the polymers used in the present invention are hydrogels which may be used in an initially dry or initially swollen state and the mode of release differs in each case. The dry crystalline gels have the particular property not possessed by rubbery gels that on swelling, for example of a cylindrical pessay of the gel by body fluids, an outer shell of swollen or rubber form is produced surrounding a core of crystalline material. This leads to certain particular advantages. Firsty, for an extended period a much more uniform release of the substance is generally achieved in vivo as compared with the usual fairly rapid exponential or $t^{-\frac{1}{2}}$ fall off found with rubbery gels. Moreover, the pattern of release is very largely controlled by the nature of the polymeric carrier rather than the nature of the entire release composition, providing the active substance has a good water solubility, so that the formulation of such release compositions to give a particular release rate is considerably simplified. In the case of active substances of low water solubility the release may be more dependent on the individual substance.

The wet gels function through the expulsion of the active substance from the release composition in a positive in vivo action consequent upon the occurrence of a rise in temperature from that at which the substance is stored and the consequent de-swelling of the polymeric carrier releasing solvent and the active substance therefrom. It will be appreciated that this necessitates the incorporation and storage of the active substance at a temperature below that to which the polymeric carrier is subjected in use. Thus, for example, when the active substance is a pharmaceutical the polymer may conveniently be treated at 20° C. or less, for example at a temperature down to 0° C. or even as low as −19° C., with the solution of the pharmaceutical to effect the desired degree of swelling and uptake of the substance. Administration of the release composition so formed to a patient will then cause the temperature to rise to body temperature, which is about 37° C. in a human, and shrinkage of the polymer then occurs with expulsion of the solvent and active substance. In the event of any problems being encountered with respect to stability of the swollen gels, it is always possible to carry out the selling shortly before use.

The present invention thus further comprises incorporating an active substance other than a prostaglandin into a polymeric carrier comprising residues of equivalent weight greater than 1,000, preferably greater than 1,500 which comprise polyethylene oxide and are cross-linked through urethane groups by swelling of the polymer at one temperature with a liquid medium containing the substance, and thereafter utilising the swollen polymer in an environment at a second, higher, temperature thereby to cause expulsion of liquid medium and active substance from the swollen polymer. Moverover, the invention comprises administering to a human or non-human animal patient a composition comprising a biologically active substance and a polymeric carrier therefor, comprising residues of equivalent weight greater than 1,000, preferably greater than 1,500, which comprise polyethylene oxide and are cross-linked through urethane groups, said composition being of a crystalline and/or swollen form.

Reference has been made previously to the desirability in some instances of removing water extractable material from the polymer. The syneresis effect provides a particularly suitable method for doing this which avoids the problems often encountered in drying down a heavily swollen polymer in an oven, for example cracking of the formed polymer. Thus, the formed polymer may be treated at a temperature below 100° C., for example at about 37° C., with water or an aqueous solvent and the swollen polymer may then be shrunk by heating in the same medium, for exaample at 100° C. in boiling water, when expulsion of solvent and dissolved soluble material will occur. Final drying may then be effected in an oven, followed by incorporation of the active substance into the polymer.

The detailed nature of the procedure used for incorporating the biologically active substance into the polymeric carrier, including the physical format of the polymeric carrier is conveniently selected with a view to achieving the desired release characteristics. The polymeric carriers may be used as film or powder but are most often used in the form of a shaped body such as a hollow or blank cylinder, a sphere, a tablet or a slab and the nature of the shape and its dimensions may be selected appropriately. The primary target is to achieve a controlled release over an appropriate time period, conveniently of a major proportion, for example 80 or 90%, of the active substance. Release at a substantially constant rate, i.e. approximating to linear release, is an appropriate target in certain instances and is provided to a considerable degree by the hydrogels of the present invention when in the form of a slab or flat sheet. Unusual release profiles may, however, be obtained by utilising polymer carriers which comprise open cavities, for example hollow cylinders or slabs with one or more holes or hollows in them. It is found that the release profiles of such polymeric carriers can go through a maximum with time. Such geometric control of release profile provides very useful additional means of obtaining and controlling improved release profiles.

It has, however, additionally been found that polymers used in the present invention generally exhibit behaviour at their upper range of swelling which can be of assistance in maintaining a rate approximating to linear release for as long a period as possible. Thus it has surprisingly been found that the polymer, once swollen by a factor of about 10 times, will typically undergo spontaneous shrinkage back to a swelling level of only about 9 times. As the dry polymer swells in use, or as the wet polymer swells further, a boost to the rate of expulsion of the active substance is thereby given just at a time when this rate may be beginning to fall.

Certain of the areas of pharmaceutical utility for compositions according to the present invention, such as the administration of hormones, drugs for the treatment of prophylaxis of various conditions, e.g. substances having activity against pathogenic micro-organisms, are particularly suited to vaginal or rectal administration of the active substance and pessaries are of especial interest in such contexts. The compositions may, however, be used for various localised application in other parts of the body such as the treatment of maladies of the mouth or eye, for example glucoma. The compositions are also of interest for oral administration or in a topical patch to release a drug which can treat or be absorbed by the skin; and for use by implantation.

The mode of release from the wet polymer carriers means that these may be employed in certain particular contexts. An example is in the treatment of maladies wherein a small dose of a drug requires to be released into the body each day. The temperature of the human body varies throughout the day, and generally follows a cycle. As the degree of swelling of the polymer is dependent on temperature, a swollen polymer carrier having a solution of a suitable drug absorbed therein may be implanted into the body, and the polymer will shrink and swell in response to the body temperature fluctuations. During the periods of shrinkage, i.e. the periods of rising temperature, increased portions of the absorbed drug will be ejected from the polymeric carrier into the bloodstream, thus providing a cyclical daily dosage of the drug.

The concentration of active substance incorporated into the controlled release composition of this invention can range from very high to very low. Thus, if a liquid biologically active material, such as m-cresol which swells the polymer to more than 1,000 pph, were used also to swell the polymer, then the active species could comprise more than 90% by weight of the release composition. A liquid which swelled to 1,000 pph and contained 25% of a drug could leave a loading of more than 70% of the drug in the dry polymer, and 30% to 70% loadings would be commonly attainable. Much lower loadings, e.g. 1.0% to 0.5% are also readily attainable.

The large degree of polymer swelling which is possible, and the small differences in temperature which occur in natural body temperature cycles, makes it possible for small doses of a drug to be positively ejected into the body daily over a long period of time, and this feature is accordingly of interest in relation to the area, for example, of long-acting contraceptives of low water solubility.

Further specific applications of the wet polymers also exist outisde the pharmaceutical field. One agricultural use is in the control of fermentation in silage. As this fermentation is accelerated by high temperature, in inhibitor which is activated by increased temperature is desirable. If swollen polyethylene oxide containing a fermentation inhibitor as the active substance is injected into the silage when the ambient temperature is low, an increase in the temperature will cause the polymer to shrink, releasing the inhibitor which then prevents or controls fermentation of the silage.

The temperature dependence of the swelling of the polymer also makes it possible for trace elements or essential growth material to be released into soil on an annual and daily basis, as a summer temperature rise will cause swollen polyethylene oxide to release a solution of such an element or material absorbed therein. Treatment of soil with a composition of the present invention may therefore be effective over a number of years, depending on the degree of release occurring through a non-syneresis mechanism.

Other uses for compositions of the present invention include the prevention of formation of slime such as algae in swimming pools by application of a slimicide (or algaecide) consequent upon the daytime temperature rise, and the inhibition of polymerisation through release of a polymerisation inhibitor in response to a temperature rise in stored polymerisable monomers. In these cases, the active substance absorbed in the swollen polyethylene oxide is a slimicide (or algaecide) and a polymerisation inhibitor respectively. Controlled release compositions of this invention, in dry form, are also of interest in relation to the beneficial effect on the storage stability of potentially unstable compounds by incorporation into a crystalline matrix.

The general advantages of the polymeric carriers used in the present invention in the formulation of active substances, as compared with other polymers described in the art for this purpose, may be summarised as follows. The polymers are non-linear, cross-linked, high equivalent weight systems of an essentially insoluble nature as regards both water and a range of organic solvents which show a high degree of swelling with both aqueous and non-aqueous solvents and form tough materials in both the dry and wet forms (although naturally to a lesser extend in the latter case). The polymeric carriers also show a good profile of release which is controlled either by the crystallinity present in the dry gels or the syneresis effect obtainable with the wet polymers.

it will be appreciated that the present invention therefore further includes a controlled release composition which comprises an active substance and a polymeric carrier therefor, the carrier comprising polyethylene oxide cross-linked through urethane groups and having the property of possessing crystallinity in the dry form and of exhibiting syneresis in the wet form. The term syneresis as used above means the property of undergoing a substantially greater level of swelling in an aqueous medium at 0° C. than at 100° C.

The invention is illustrated by the following Examples.

Preparation of Polymers

EXAMPLE 1

Polyethylene oxide/methane diphenyl di-isocyanate/trimethylol propane polymer

Polyethylene glycol (PEG (6,000, supplied by ICI) is melted and passed through a charcoal column at 80° C. in order to remove acidic contaminants. The product is then dried at 120° C. for 6 hours under vacuum whilst bubbling dry nitrogen through the melt in order to assist the removal of water. The hydroxyl and acid numbers are then determined by the method described in the ASTM (American Society for Testing Materials) Manual D1638, 67T, numbers 93 to 118 to give values of 18.85 and 0.70 respectively (hydroxyl number corrected using acid number=19.55). Using this corrected hydroxyl number the stoichiometric equivalent of 4,4'-diphenyl-methane di-isocynate (MDI) for 6,000 grams of the product is calculated to be 1.05 moles or 262.5 g.

Purified PEG 6,000 (280.04 g) is treated at 80° C. in a round bottom flask with 2-ethyl-2-hydroxymethylpropane-1,3-diol (trimethylol propane, TMP, supplied by BDH) which has been dried under vacuum (1 mm Hg) at 80° C. for 6 hours and thereafter stored in a desiccator. Pure molten MDI (supplied by ICI and purified by distillation at 2 mm Hg) is added to the mixture of glycols. The whole mixture is briefly stirred for 15 seconds and is then degassed for 2 minutes before pouring into a suitable preheated mould for curing by heating in an oven. The cured polymer, which is an opaque white mass, is stored in the absence of water.

Several molar proportions of TMP are used in the preparation of different polymers. The respective amounts of TMP are 3.13 g, 4.695 g and 6.26 g (0.5, 0.75 and 1.0 molar proportions). The amount of MDI used in each case is 1.05 molar proportions in respect of the PEO and 1.5 molar proportions in respect of the triol. The quantity will accordingly vary, depending on the molar proportion of triol/PEO, the amounts being respectively 21.15g, 25.5 g and 29.75 g of MDI (1.8, 2.175 and 2.55 molar proportions relative to PEO) for 0.5, 0.75 and 1.0 molar proportions of triol relative to PEO.

EXAMPLE 2

Polyethylene oxide/methane diphenyl di-isocyanate/1,2,6-hexane triol polymer

The procedure described above for the PEO/MDI/TMP polymer is followed but using the following reactants:
polyethylene glycol (PEG 6,000): 313.41 g
1,2,6-hexane triol: 6.7 g (1 molar proportion)
4,4'-diphenylmethane di-isocyanate: 33.3 g (2.55 molar proportions)

The cured polymer is obtained in an exactly analogous fashion.

EXAMPLE 3

Polyethylene oxide/methane diphenyl di-isocyanate/phloroglucinol polymer

The procedure described above for the PEO/MDI/TMP polymer is followed but using the following reactants.
polyethylene glycol (PEG 6,000): 301.4 g
phloroglucinol: 6.329 g (1 molar proportion)
4,4'-diphenylmethane di-isocynate: 32.023 g (2.55 molar proportions)

The cured polymer is obtained in an exactly analogous fashion.

EXAMPLE 4

Polyethylene oxide/methane diphenyl di-isocyanate polymer (A) Polyethylene glycol (325.25 g, PEG 6,000) purified as described previously is placed in a beaker at 80° C. and crude MDI (total of 21.24 g corresponding to the stoichiometric equivalent required by the glycol of 16.34 g plus an excess of 4.9 g, being 30% of this amount, supplied by ICI as Suprasec-DN) is added to it whilst maintaining the temperature close to 80° C. and with continuous stirring. Once the addition is complete the homogeneous mixture is poured into a suitable preheated mould for curing by heating in an oven. The cured polymer, which is a dark brown mass, is stored in the absence of water.

(B) The procedure described under (A) above is repeated but using polyethylene glycol (PEG 4,000, supplied by ICI) which is purified as described previously for PEG 6,000, having a hydroxyl number of 27.11, an acid number of 0 and a corrected hydroxyl number of 27.11.

The following proportions of reactants are employed:
polyethylene glycol: 251.47 g
crude MDI: 22.71 g
(stoichiometric equivalent of 17.47 g plus the 30% excess of 5.24 g)

The cured polymer is obtained in an exactly analogous fashion.

Example 5 to 7 below illustrate the reduction in crystallinity in the dry gel with decreasing equivalent weight. The preparative method was in all cases analogous with the following procedure referred to #3 of Example 5.

1.615 g of 1,2,6-hexanetriol is added to 100 g of polyethylene oxide of number average molecular weight 8300 (Carbowax 6000 ex Union Carbide) in a beaker and both are allowed to stand at 80° C. 7.527 g of pure molten MDI is then poured into the mixture which is then vigorously stirred for 30 seconds before being poured into a mould which was preheated at 85° C. The mount is placed in, an oven at 85° C. for four hours to cure. After curing the mould is next cooled and the opaque off-white block of polymer was removed and stored away from moisture.

EXAMPLE 5

| Moles thiol[1] moles PEO[2] | Wt. (g) PEO | Wt. (g) triol | Wt. (g) MDI | Physical appearance |
| --- | --- | --- | --- | --- |
| 0.5 | 100 | 0.8075 | 5.2705 | white brittle |
| 0.75 | 100 | 1.2113 | 6.3992 | Opaque |
| 1.0 | 100 | 1.615 | 7.527 | Opaque |
| 1.25 | 100 | 2.0189 | 8.6363 | Opaque |
| 1.5 | 100 | 2.4227 | 9.7848 | Opaque |
| 1.75 | 100 | 2.826 | 10.9119 | Opaque |
| 2.0 | 100 | 3.23 | 12.041 | Opaque |
| 3.0 | 100 | 4.8454 | 15.5556 | Opaque |
| 4.0 | 100 | 6.460 | 21.068 | Almost transparent |

EXAMPLE 6

| Mole triol[1] moles PEO[3] | Wt. (g) PEO | Wt. (g) triol | Wt. (g) MDI | Physical appearance |
| --- | --- | --- | --- | --- |
| 0.25 | 100.0 | 1.0437 | 10.73044 | Opaque |
| 0.35 | 120.0 | 1.8305 | 14.5853 | Opaque rubbery |
| 0.5 | 100.0 | 2.092 | 13.6525 | Opaque rubbery |
| 0.75 | 100.0 | 3.137 | 16.5752 | rubbery |
| 1.0 | 100.0 | 4.184 | 19.4978 | Slightly transparent |
| 1.25 | 100.0 | 5.2284 | 22.4197 | Slightly transparent |
| 1.5 | 120.0 | 7.529 | 30.4112 | transparent |
| 1.75 | 100.0 | 7.3219 | 28.2755 | transparent |
| 2.0 | 100.0 | 8.368 | 31.1989 | transparent |

EXAMPLE 7

| Moles triol[1] moles PEO[4] | Wt. (g) PEO | Wt. (g) triol | Wt. (g) MDI | Physical appearance |
| --- | --- | --- | --- | --- |
| 0.3 | 100.0 | 2.5002 | 22.532 | Opaque rubbery |
| 0.4 | 100.0 | 3.3336 | 24.8697 | Opaque rubbery |
| 0.5 | 100.0 | 4.1675 | 27.1984 | Transparent rubbery |
| 0.6 | 100.0 | 5.0004 | 29.5278 | Transparent rubbery |
| 0.75 | 100.0 | 6.2506 | 33.0219 | Transparent rubbery |
| 1.0 | 100.0 | 8.3341 | 38.8447 | Transparent rubbery |
| 1.25 | 100.0 | 10.4177 | 44.6679 | Transparent rubbery |
| 1.5 | 100.0 | 12.5012 | 50.4908 | Transparent rubbery |
| 1.75 | 100.0 | 14.5847 | 56.3138 | brittle |
| 2.0 | 100.0 | 16.6682 | 62.136 | brittle |

[1] triol is 1, 2, 6-hexanetriol
[2] PEO is Carbowax 6,000 (Union Carbide) $M_n$ = 8300
[3] PEO is Carbowax 4000 (Union Carbide) $M_n$ = 3200
[4] PEO is Carbowax 1,500 (Union Carbide) $M_n$ = 1600

Examples 8 and 9 below illustrate the preparation of polymers using aliphatic di-isocynates. These are hexamethylene di-isocyanate (ex Bayer) and methane dicyclohexane di-isocyanate (Hylene W ex Du Pont). A catalyst, in this cse from 0.4 to 0.6% w/w FeCl$_3$, was used to lower the reaction time.

EXAMPLE 8

| Moles triol[1] mole PEO[2] | Wt. (g) PEO | Wt. (g) triol | Wt. (g) Hylene | Wt. (g) Hexamethylene di-isocyanate |
|---|---|---|---|---|
| 0.5 | 100 | 1.61 | 7.91 | — |
| 0.5 | 100 | 1.61 | — | 5.06 |
| 0.75 | 100 | 1.21 | 6.72 | — |
| 0.75 | 100 | 1.20 | — | 4.30 |
| 1.00 | 100 | 0.81 | 5.53 | — |
| 1.00 | 100 | 0.81 | — | 3.50 |

EXAMPLE 9

| Moles triol[1] moles PEO[3] | Wt. (g) PEO | Wt. (g) triol | Wt. (g) Hylene | Wt. (g) Hexamethylene di-isocyanate |
|---|---|---|---|---|
| 0.5 | 100 | 2.092 | 14.329 | — |
| 0.5 | 100 | 2.092 | — | 9.174 |
| 0.75 | 100 | 3.138 | 16.956 | — |
| 0.75 | 100 | 3.138 | — | 10.856 |
| 1.0 | 100 | 4.184 | 19.879 | — |
| 1.0 | 100 | 4.184 | — | 12.727 |

EXAMPLE 10

Polymer incorporating diphenydramine hydrochloride

A polymer, prepared as described in Example 1 above using 0.75 molar proportions of TMP is poured at 80° C. into a preheated mould consisting of polythene tubing and then cured by heating in an oven at 80° C. for 20 hours. After cooling, the mould is cut away to give a long opaque white cylinder of the polymer which is cut into pieces of suitable length.

The small cylinders are then treated to extract the bulk of the water extractable fraction contained therein by swelling them in a 7:3 v/v ethanol/water mixture for 120 hours at ambient temperature and then drying under vacuum at ambient temperature. It is typically found that a cylinder of original weight 0.67 g is reduced to a weight of 0.46 g after going through the swelling and drying cycle.

The re-dried cylinders are next swelled for 48 hours at ambient temperature using a solution of 10 mg/ml of diphenydramine hydrochloride in distilled water, typically giving a cylinder of wet weight 3.88 g corresponding to an uptake of 3.42 g of the solution or 34.2 mg of diphenydramine hydrochloride. The swollen cylinder is dried under vacuum at ambient temperature.

In vitro studies on the release of diphenyhydramine hydrochloride from the dry cylinders into water through mesurement of the absorence at 258 nm typically show a half life which is of the order of 1.8 hours although the exact value will depend on the dimensions of the cylinder.

In ariants of the above procedure one of the polymers prepared as described in Examples 2 to 4 above is substituted for the polymer.

EXAMPLE 11

Polymer incorporating aspirin

A polymer prepared as described in Example 1 above using 0.5 molar proportions of TMP is poured at 85° C. into a rectangular mould and then cured by heating in an oven at 85° C. for 16 hours. After cooling the opaque white block of polymer is removed from the mould and cut into smaller blocks. The small blocks of the polymer are swelled for 48 hours at ambient temperature using a solution of 1 g of aspirin in mixture of 7 g of ethanol and 7 g of 0.1N aqueous sulphuric acid, typically giving an increase in weight in the blocks of 2.115 g from 0.334 g dry weight to 2.443 g wet weight, corresponding to an uptake of 141 mg of aspirin by a block. The blocks are rinsed briefly with distilled water and dried under vacuum at ambient temperature for 3 days.

In vitro studies on the release of aspirin from the dry blocks into 0.1N aqueous sulphuric acid at 37° C. through measurement of the absorbence at 231 nm typically show a half life for release of the drug which is of the order of 6 hours although the exact value will depend on the dimensions of the block.

In variants of the above procedure one of the polymers prepared as described in Examples 2 to 4 above is substituted for the polymer.

EXAMPLE 12

Polymer incorporating promethazine hydrochloride

A small block of polymer is prepared as described in Example 2. It is then cut to form slabs (1 mm×6 mm×20 mm). The slabs are next extracted and dried as described in Example 10. Promethazine hydrochloride is then incorporated into the polymeric carrier by swelling it for 48 hours at 37° C. using a solution of 1.0% w/v of the drug in 0.007N HCl. The loaded slabs (5.12% w/w dry) are then dried under vacuum at 40° C. for 48 hours.

In vitro studies on the release of promethazine hydrochloride are thereafter effected at 37° C. in 1,000 ml of 0.001N HCl to maintain sink conditions. It is found that a uniform release is obtained until about 50% of the promethazine hydrochloride has been delivered, which took about 150 minutes.

EXAMPLE 13

Polymer incorporating caffeine

Extracted slabs prepared as in Example 12 were swollen in 1% w/v of caffeine in phosphate buffer (pH=7.4) at 37° C. for 48 hours.

In vitro studies on the release of caffeine from the dried slabs showed that a uniform release of the caffeine is obtained, similar to the profile obtained in Example 12.

EXAMPLE 14

Polymer incorporating methatrexate

Extract slabs prepared as in Example 12 were swollen in 2.5% w/v of methatrexate in 0.01N NaOH at 37° C. for 48 hours.

In vitro studies on the release of methatrexate from the dried slabs showed that a uniform release of methatrexate is obtained into a buffer solution of pH 6.0.

EXAMPLE 15

Polymer containing bovine serum albumen

Extracted slabs prepared as in Example 12 were swollen in a 2% standard solution of albumen (crystallised and lyophilised) in a phosphate buffer at 37° C. for 48 hours.

In vitro studies on the release of albumen were made at pH=7.4 and 37° C.

We claim:

1. A controlled release composition comprising an active substance other than a prostaglandin, and a polymeric carrier therefore comprising residues which are cross-linked through urethane groups, or analogues thereof, and which comprise polyethylene oxide having a ratio of number average molecular weight to functionality greater than 1,500, the degree of cross-linking being such that there is at least one cross-linking point per ten residues comprising the said polyethylene oxide but such that the proportion of the said polyethylene oxide is greater than 50% by weight of the polymeric carrier which is a crystalline hydrogel in the dry form and exhibits syneresis in the wet form.

2. The controlled release composition according to claim 1, wherein the polyethylene oxide has a ratio of number average molecular weight to functionality greater than 2,000.

3. The composition according to claim 1, wherein the polyethylene oxide is the reaction product of a mixture comprising:
   (i) an aliphatic or aromatic compound which is di-, tri- or tetrasubstituted by at least one of hydroxyl, carboxyl, amino or mercapto groups with (ii) ethylene oxide.

4. The composition according to claim 3, wherein:
   (i) comprises a di- or tri- hydroxyl-substituted aliphatic compound.

5. The composition according to claim 1, wherein the degree of cross-linking of the polymeric carrier is such that there is at least one cross-linking point per five residues comprising the said polyethylene oxide.

6. The composition according to claim 1, wherein the degree of cross-linking of the polymeric carrier is such that there is at least one cross-linking point per residue comprising the said polyethylene oxide.

7. The composition according to claim 1, wherein the degree of cross-linking of the polymeric carrier is such that the proportion of the said polyethylene oxide is greater than 70% by weight of the polymeric carrier.

8. The composition according to claim 1, wherein the degree of cross-linking of the polymeric carrier is such that the proportion of the said polyethylene oxide is greater than 80% by weight of the polymeric carrier.

9. The composition according to claim 1, wherein the polymeric carrier comprises up to 20% by weight of an additional polyalkylene oxide.

10. The composition according to claim 1, wherein the polymeric carrier comprises up to 20% by weight of an additional polyethylene oxide having a ratio of number average molecular weight to functionality not greater than 1000.

11. The composition according to claim 1, wherein the polymeric carrier comprises up to 30% of its weight of a water-extractable fraction.

12. The composition according to claim 11, wherein the amount of water-extractable fraction has been reduced to no more than 5% of the polymeric carrier.

13. The composition according to claim 1, wherein the drug is a hypnotic, sedative, tranquilliser, antipyretic, anti-inflammatory agent, anti-histamine, anti-tussive, agent for the treatment of malignant neoplastia, topical or dermatological agent, diuretic agent, anti-depressant, anti-fungal agent, steriod or analgesic.

14. The composition according to claim 1, in the shape of a cylinder, film or slab.

15. The composition according to claim 14, wherein the cylinder is hollow or the film or slab has at least one hole or hollow therein to modify the release properties.

16. The composition according to claim 1, wherein the active substance comprises a fungicide, algaecide, herbicide, nematocide or insecticide.

17. The composition according to claim 1, wherein the active substance is lithium.

18. The composition according to claim 1, wherein the active substance comprises a polymerization inhibitor.

* * * * *